United States Patent [19]
Rusz et al.

[11] Patent Number: 5,230,331
[45] Date of Patent: Jul. 27, 1993

[54] HOT WIRE ANEMOMETER ADAPTED FOR INSERTION IN A CALIBRATION SOCKET OF A PULMONARY GAS FLOW MONITOR

[75] Inventors: Tibor Rusz, Albuquerque, N. Mex.; Elliott Jacobson, Pasadena, Calif.; Jon R. Bryan, Albuquerque, N. Mex.

[73] Assignee: R. J. Instruments, Albuquerque, N. Mex.

[21] Appl. No.: 797,388

[22] Filed: Nov. 25, 1991

Related U.S. Application Data

[62] Division of Ser. No. 554,690, Jul. 19, 1990, Pat. No. 5,094,246.

[51] Int. Cl.$^5$ .............................................. A62B 7/00
[52] U.S. Cl. .................................. 128/205.23; 128/724
[58] Field of Search ................... 128/716, 724, 202.22, 128/205.23

[56] References Cited

U.S. PATENT DOCUMENTS

| | | | |
|---|---|---|---|
| 3,962,917 | 6/1976 | Terada | 128/724 |
| 4,163,390 | 8/1979 | Rodder | 128/724 |
| 4,363,238 | 12/1982 | Willam | 128/724 |
| 5,094,246 | 3/1992 | Rusz et al. | 128/724 |

*Primary Examiner*—Edgar S. Burr
*Assistant Examiner*—Aaron J. Lewis

[57] ABSTRACT

A hot wire sensor has a cylindrical light-transparent tube having two opaque patches adjacent the two tube ends, respectively, and with one platinum "hot" wire mounted about centrally therein and another platinum wire mounted adjacent thereto. A gas flow monitor includes a resistive bridge circuit, connected to the hot wire sensor. In the bridge circuit, the two platinum wires become two of the adjacent bridge branches. A DC voltage supply of the monitor is connected across the bridge at the bridge junction of the platinum wires, heating the one but not the other owing to disparate resistances in the bridge branches. A calibration socket is mounted vertically on an outer wall of the monitor housing. To calibrate the sensor, a tube end is inserted into the socket holding the tube axis horizontal and the tube is rotated until the opaque patch breaks a light beam between a LED and a photo transistor at the periphery of the socket. At that position the one "hot" wire is horizontal and the breaking of the light beam electrically enables (unlocks) the bridge so that an adjustment of one of the bridge arm resistances can be made to obtain a bridge output voltage of predetermined value corresponding to zero flow of gas through the sensor tube.

2 Claims, 1 Drawing Sheet

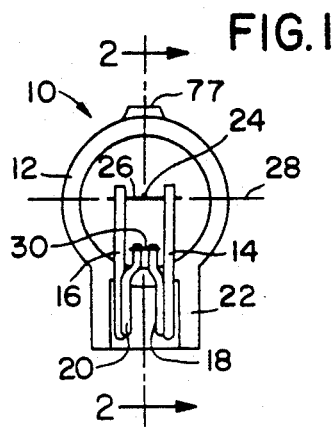
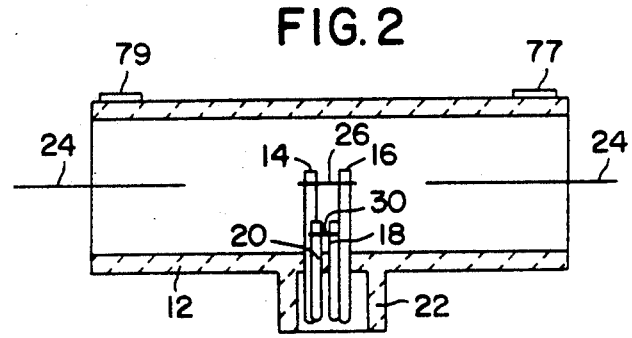
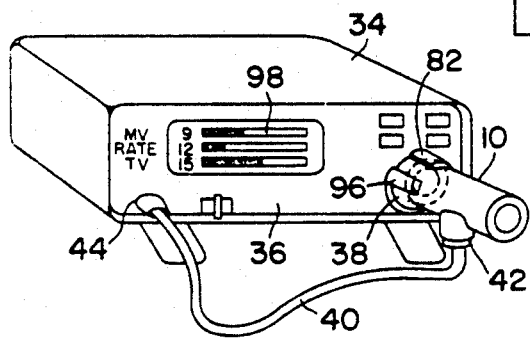
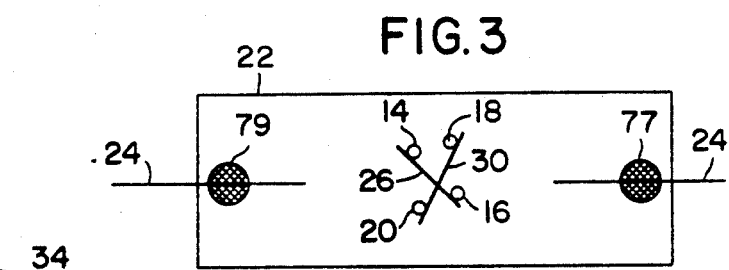
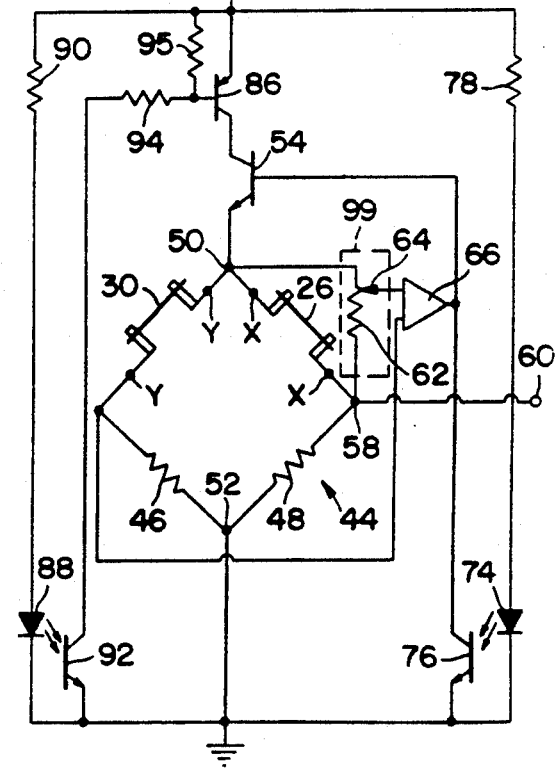
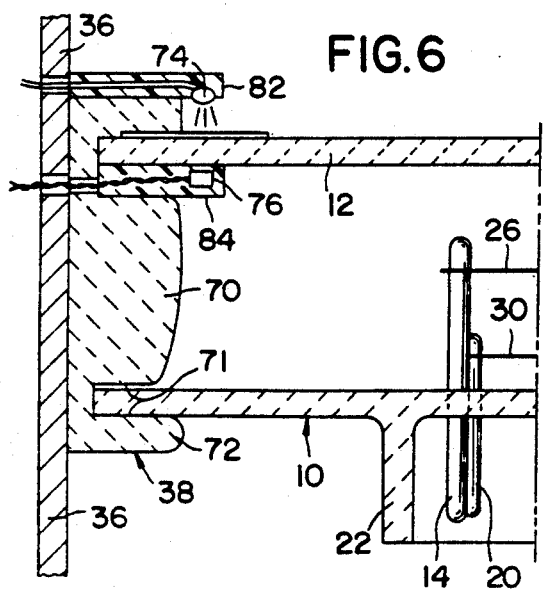

HOT WIRE ANEMOMETER ADAPTED FOR INSERTION IN A CALIBRATION SOCKET OF A PULMONARY GAS FLOW MONITOR

CROSS REFERENCE TO RELATED APPLICATION

This application is a division of application Ser. No. 07/554,690, filed Jul. 19, 1990 now U.S. Pat. No. 5,094,246.

BACKGROUND OF THE INVENTION

This invention relates to gas flow rate monitors employing hot wire anemometer sensors, and more particularly to such a monitor enabling a fast, accurate and reliable means of calibrating each hot wire sensor.

Gas flow rate monitors equipped with hot wire anemometer sensors are especially suitable for use in making continuous measurements of gas flow rate in the breathing system of an anesthetized and paralyzed patient whose breathing must be assisted by ventilator machinery such as those described in U.S. Pat. No. 4,637,385 issued Jan. 20, 1987 and U.S. Pat. No. 4,581,945 issued Apr. 15, 1986. From a gas flow rate measurement, other important information such as tidal volume and minute volume may be calculated. The hot wire anemometer for this critical purpose is much preferred over other known sensors such as the rotary vane sensor, the Pitot tube, differential pressure drop sensor across a laminar flow element or across other gas-flow resistance elements such as wire screen, ultrasonic sensors, heat transfer sensors, and thermistors.

Hot wire sensors, usually employing platinum wires and the associated instrumentation are capable of stable reliable operation when subjected to the rough handling and harsh environment to which pulmonary gas flow monitors are typically subjected. Hot wire sensors for use in measuring the flow of a patient's breath are preferably made by mounting the wires in a cylindrical light-transparent tube so that it can be readily observed when blood, vomit or any other body fluids that pass through the tub indicating what trouble the patient may have, and alerting the doctor that such body fluids may collect on the platinum wire throwing the sensor out of calibration.

A gas flow monitor with hot-wire sensor is described by Rusz et al in the U.S. Pat. No. 3,913,379 issued Oct. 21, 1975. This gas flow monitor has a resistor bridge with two adjacent branches that consist respectively of a remotely connected pair of platinum wires that are mounted in the tube of the hot-wire sensor. Calibration of each hot wire sensor is accomplished by changing the balance of the bridge using a high resistance potentiometer connected across one branch of the bridge to obtain under zero gas flow conditions a bridge output voltage of a predetermined value.

That setting of the potentiometer is to remain fixed during ensuing flow measurements that are made using that particular sensor. Hot wire sensors vary from one to the other and each must be individually calibrated before use.

During the calibration procedure it is important that the cylindrical tube of the sensor be blocked at least at one end so that no air may flow through the tube. Also during the calibration it is necessary that the tube remain horizontal, because otherwise the hot platinum wire will cause convective air currents within the tube leading to an erroneous calibration of the zero-air-flow state.

The later two conditions for assuring zero air flow during calibration are particularly important since the sensitivity of hot wire sensors is greatest for zero flow and dimishes substantially as air flow increases. Thus it is customary to manually hold the sensor tube about horizontal while plugging one or both tube ends. This manual handling is clumsy and tends to be done only approximately adversely affecting the calibration accuracy.

It is therefore an object of this invention to provide an improved hot wire gas flow sensor capable of being easily blocked and oriented properly during calibration.

It is a further object of this invention to provide a gas flow monitor enabling a simpler more reliable procedure for accurate calibration of hot-wire sensors.

SUMMARY OF THE INVENTION

A respiratory hot wire anemometer sensor is comprised of a transparent cylindrical tube in which a pair of electrically conductive loads are mounted in and through a wall of the tube. A "hot" platinum wire is connected about in the center of the tube between the pair of leads. The tube has an opaque region or patch adjacent one tube end.

A respiratory gas flow monitor includes this sensor and means for providing a heating current to the platinum wire and for generating an electrical signal that is directly related to the change in voltage across the platinum wire due to the flow of gas through the tube and over the platinum "hot" wire, and thus directly related to the rate of the gas flow itself.

Each such respiratory hot wire anemometer sensor must be accurately calibrated before use. The gas flow monitor of this invention has a sensor calibration-socket means mounted in a wall of the housing containing the electrical signal generating means. The socket means is for accepting and holding the sensor tube by the one end thereof with the axis of the tube in a horizontal position and with the one tube end blocked so that gas flow through the tube cannot exist. A flexible electrical cable or other means electrically connects the "hot" platinum wire to the circuit means.

Other features of the monitor include one light path detecting means that detect the opaque region of the sensor when the tube is rotated in the socket means to simultaneously position the platinum "hot" wire horizontally and to place the opaque tube-region at the location of the light path detecting means. The logic signal output of the light path detecting means is connected to a circuit locking means which disables the signal generating means when the light path is not blocked, and enables the signal generating means when the sensor tube is properly oriented to block the light path detecting means.

Another light path detecting means located at a different point at the circumference of the socket means provides a logic signal to the input of a circuit enabling means to enable the signal generating means only when the sensor tube inserted into the calibration socket means is a transparent one.

The respiratory hot wire anemometer sensor and pulmonary gas flow monitor of this invention removes elements of operator judgement in the process of calibrating each anemometer sensor and insures a disciplined, more reliable and thus safer sensor calibration procedure.

BRIEF DESCRIPTION OF THE DRAWING

FIG. 1 shows in end view a hot-wire gas-flow sensor of this invention.

FIG. 2 shows in side sectional view the sensor of FIG. 1 taken in plane 2—2.

FIG. 3 shows in top view the sensor of FIG. 1.

FIG. 4 shows in perspective view the gas flow monitor of this invention including the hot-wire gas-flow sensor of FIG. 1.

FIG. 5 shows the preferred embodiment of a circuit of the monitor of FIG. 4 including interalia the "hot" platinum wire of the sensor of FIG. 1.

FIG. 6 shows an enlarged detail in side sectional view of the sensor socket of FIG. 4 for holding the sensor by one tube end, taken in vertical plane 2—2.

DESCRIPTION OF THE PREFERRED EMBODIMENT

A hot-wire, gas-flow sensor 10 as shown in FIGS. 1, 2 and 3 includes a cylindrical light-transparent plastic tube 12 having mounted therein four about mutually parallel lead wires 14, 16, 18 and 20. These lead wires extend outwardly of the tube 12 about radially relative to the cylindrical tube 12. A protective cylindrical tube 22 surrounds and physically protects the radially extending lead wires 14, 16, 18 and 20. The view of the sensor is straight into the axis 24 of the tube 12.

The platinum wire 26 is connected between lead wires 14 and 16 and positioned about horizontally in plane 28 that includes the axis 24 of the tube. This is the preferred position for the "hot" wire 26 that is to be heated so that convection air currents from a lowest end of the heated wire 26 do not further heat the higher wire end.

A platinum wire 30 is connected between lead wires 18 and 20 adjacent the "hot" wire 26 but near the inner wall of the tube 12. Its function as a temperature compensating element is described in the above-noted patent U.S. Pat. No. 3,913,379.

Referring to FIG. 4, a cabinet or housing 34 has mounted in a front panel 36 thereof a socket 38. The hot-wire gas-flow sensor 10 is shown plugged into and horizontally held by the socket 38. A flexible multi-wire electrical cable 40 has at one end a female multiple pin receptacle 42 pushed onto the distal ends of wire leads 14, 16, 18 and 20, connecting them respectively to four terminals in an electrical connector 44 which four terminals are identified in FIG. 5 as the two points designated X and the two points designated Y. Between the two terminals X as shown in FIG. 5, the "hot" platinum wire 26 is connected (via cable 40). Between the terminals Y the platinum wire 30 is connected (also via cable 40).

Platinum wires 26 and 30 are the resistive elements, respectively, in first and second branches of a resistive bridge circuit 44. The third and fourth branches are resistors 46 and 48. A DC voltage is provided across energizing nodes 50 and 52 of the bridge circuit 44 via a transistor 54 from a DC voltage source 56. The resistance of the bridge resistor 46 is at least one order of magnitude greater than bridge resistor 48 so that the amount of current through platinum wire 26 is about that much greater than that through temperature compensating platinum wire 30. The voltage across the bridge is normally about 5 volts where +V is 15 volts. The output node 58 of the bridge 44 is connected to output conductor 60. The output signal voltage $V_F$ at conductor 60 is a positive non-linear function of the rate of flow of gas through the gas-flow sensor 10, taken relative to grounded bridge node 52.

A high resistance potentiometer 62 (high relative to the "hot" wire resistance of 15 ohms) is connected across "hot" wire 26. The variable arm of potentiometer 62 is connected to the output of the voltage amplifier 66. Potentiometer arm 64 can now be adjusted to change the output voltage $V_F$ to a predetermined voltage, e.g. 1.00 volt, when there is not air flow in order to calibrate a sensor 10 prior to making gas flow rate measurements.

Referring now to FIG. 6, the sensor socket 38 is comprised of a central plug portion 70 and an outer ring portion 72 forming together a circular groove 71 into which one end of sensor tube 12 may be snugly inserted to hold the tube 12 in a horizontal position and to stop passage of any air through the tube during the calibration procedure. The tube 12 may be rotated in groove 71 while being held horizontal therein. Socket 38 additionally includes a lamp 74 and a light sensor 76 mounted at an outer wall and opposite the inner wall of the end of sensor tube 12 that is held by socket 38.

Referring to FIG. 5 again, the lamp or LED 74 is connected in series with a current limiting resistor 78 to the voltage source 56 so as to energize the LED 74. The resulting illumination shining on the photo transistor 76 causes transistor 76 to be conductive turning off transistor 54 and disabling the bridge 44. Thus the bridge 44 is held deenergized and disabled (1) when no sensor 10 is plugged into the socket 38 and (2) when a sensor 10 is plugged into and held by socket 38 where a transparent portion thereof is located between LED 74 and photo transistor 76.

However, referring again to FIGS. 1, 2 and 3, the sensor 10 has adjacent the ends thereof opaque patches 77 and 79. Then a sensor 10 is rotated in the socket 38 until the opaque patch, e.g. 79, interrupts the light from the LED 74 to the photo transistor 76, transistor 76 turns off and the bridge becomes operative and ready for calibration of the blocked horizontally held sensor 10. A first cantilevered plastic shroud 82 extends from the outer ring portion 72 of socket 38 and houses the LED 74. A second shroud 84 extends from the central plug portion 70 and houses the photo transistor 76, holding it adjacent to and illuminated by the LED 74 when the socket is empty.

The opaque patches 77 and 79 of the tube 12 are located directly over the "hot" wire 26 when looking down the tube axis 24 as seen in FIG. 1. Also the LED 74 and photo transistor 76 are located at the very top of the socket 38 perimeter as illustrated in FIGS. 4 and 6. Thus when either end of the tube 12 is inserted into the groove 71 of socket 38 and rotated until the opaque region 77 (or 79) blocks the light path from LED 74 to photo transistor 76, the bridge 44 is energized only for this preferred rotational position of tube 12 at which the hot wire 26 is both horizontal and is situated above the temperature-compensating platinum wire 30. At 180° rotation of the tube the "hot" wire 26 would be horizontal, but convection current from the "hot" wire 26 would be heating the wire 30 lying above it and cause a calibration error.

Also in FIG. 5 is shown a transistor 86 connected in series between the bridge circuit 44 and the DC voltage supply 56. A second lamp, LED 88, is energized by the voltage supply 56 through current limiting resistor 90 and normally irradiates photo transistor 92 connecting when conducting the base of transistor 86 through base-current-limiting resistor 94 to ground to hold on transistor 86. Otherwise the base of transistor 86 is held at V+ through resistor 95 turning off transistor 86 when the light path from LED 88 to phototransistor 92 is blocked by an opaque sensor tube in socket 38.

The sensor socket 38 additionally includes a third shroud 96 cantilevered from the outer socket ring portion 72, as was the first shroud 82 except at a different position on ring portion 72. A fourth shroud (not seen) identical to shroud 84 extends from the central plug portion 70 adjacent the shroud 96. Also just as with shrouds 82 and 84, the third (96) and fourth shrouds house a co-reacting LED (88) and photo transistor 95.

When the socket is empty light from LED 88 turns on photo transistor 92. When an end of the tube 12 of a hot wire gas flow sensor 10 is plugged into socket 38 and rotated so that the opaque patch (77 or 79) blocks light from LED 74 to photo transistor 76, then the transparent portion of the tube 12 between LED 88 and photo transistor 92 allows photo transistor 92 to turn on, thereby turning on transistor 86 and calibration can now proceed. However, when a hot wire sensor tube of the kind that is totally opaque is plugged into socket 38, transistor 86 turns off the bridge and calibration of such an opaque sensor cannot ensue. This safety feature mitigates against use of older less safe opaque sensors.

The output signal appearing at conductor 60 and having an amplitude representing, for example, the rate of flow of a patient's inspiratory breathing gasses, can now be manipulated in known ways. If tidal volume is wanted, the integral of the output voltage at conductor 60 over each breathing period can be performed by known means and displayed, e.g. in bar graph form on the CRT display 98 of FIG. 4. Likewise, breathing rate and minute volume can be derived from the output voltage at conductor 60.

The potentiometer 64 may be replaced by an all solid state, no-moving parts, electronic variable resistor and logic circuit that will perform exactly the same function as will the manually adjusted potentiometer 64. With little more complexity, that electronic circuit represented by the block 99 of dashed lines in FIG. 5 can also sense when a hot-wire anemometer sensor 10 is plugged in and properly oriented for energizing the bridge 44 by noting when a DC voltage appears at junction 50 and thereupon automatically initiating the calibration procedure and establishing the shunting resistance across hot-wire 26 appropriate to the characteristics of that particular hot-wire sensor 10.

When calibration is complete, the calibrated sensor 10 is simply removed from the socket 38 and inserted in series with the expiratory branch of the breathing system of a patient. Removal from socket 38 will result in turning on transistor 76 as has been described. Some other means (not shown) need be employed to turn off transistor 76 during subsequent use of the calibrated sensor for measuring the expiratory breathing gas flow of a patient.

What is claimed is:

1. A respiratory hot-wire anemometer sensor comprising a transparent cylindrical tube; a first pair and a second pair of electrically conductive leads extending about radially from within said tube and sealingly through the wall of said tube; one and another platinum wires, the ends of each of said platinum wires connected within said tube respectively between said first pair and said second pair of said leads, said tube having adjacent one end and on a cylindrical surface thereof one opaque patch and having adjacent the opposite end and thereof on a cylindrical surface another opaque patch, said opaque patches having the same circumferential orientation about said tube end each of said opaque patches extending only partially around said cylindrical surface so as to permit the patches to be moved into and out of alignment with associated structure by rotation of said cylindrical tube.

2. A respiratory hot-wire anemometer sensor comprising a transparent cylindrical tube; a first pair and a second pair of electrically conductive leads extending about radially from within said tube and sealingly through the wall of said tube; one and another platinum wires, the ends of each of said platinum wires connected within said tube respectively between said first pair and said second pair of said leads, said tube having adjacent one end and on a cylindrical surface thereof one opaque patch, said opaque patch extending only partially around said cylindrical surface so as to permit the patch to be moved into and out of alignment with associated structure by rotation of said tube.

* * * * *